United States Patent [19]

Klemann

[11] Patent Number: 4,590,288

[45] Date of Patent: May 20, 1986

[54] BI- OR POLYMETALLIC COORDINATION COMPLEX

[75] Inventor: Lawrence P. Klemann, Somerville, N.J.

[73] Assignee: Exxon Research and Engineering Co., Florham Park, N.J.

[21] Appl. No.: 508,937

[22] Filed: Jun. 29, 1983

[51] Int. Cl.$^4$ .......................... C07F 1/08; C07F 15/02; C07F 15/04

[52] U.S. Cl. ........................................ 556/112; 556/7; 556/114; 556/122; 556/137; 556/141; 546/2; 546/5; 549/3; 564/372

[58] Field of Search ............... 260/438.1, 429 J, 429.5, 260/438.5 R, 439 R, 429.9, 430; 546/2, 5; 549/3; 564/372

[56] References Cited

U.S. PATENT DOCUMENTS

| | | | |
|---|---|---|---|
| 2,794,817 | 6/1957 | Bersworth | 260/429 J |
| 2,977,279 | 3/1961 | Kosmin | 260/429 J |
| 3,678,000 | 7/1972 | Adams | 260/429 J X |
| 3,755,447 | 8/1973 | Klemann et al. | 260/429 J X |
| 3,758,580 | 9/1973 | Lancer et al. | 260/429 J X |
| 4,268,455 | 5/1981 | Langer et al. | 260/429 J X |
| 4,337,335 | 6/1982 | Nagabhushan et al. | 260/429 J X |

FOREIGN PATENT DOCUMENTS

| | | |
|---|---|---|
| 1448025 | 8/1966 | France . |
| 6513852 | 4/1966 | Netherlands . |

OTHER PUBLICATIONS

Chemical Abstracts 99:81502j (1983).
Chemical Abstracts 93:196878e (1980).
Chemical Abstracts 81:20349w (1974).
Gagne et al., *J.A.C.S.*, 101, 4571–4580 (1979).
Drew et al., *J.C.S. Dalton*, 1868–1878 (1981).
Drew et al., *J.C.S. Chem. Comm.*, 388–389 (1981).
Gagne et al., *J.A.C.S.*, 99, 8367–8368 (1977).
Sorrell et al., *Inorg. Chem.*, 21, 3250–3252 (1982).
Sorrell et al., *J.A.C.S.*, 104, 2054–2056 (1982).
Drew et al., *J.C.S. Chem. Comm.*, 829–831 (1980).
Karlin et al., *J.C.S. Chem. Comm.*, 881–882 (1981).
Karlin et al., *J. Coord. Chem.*, 11, 61–63 (1981).
Karlin et al., *J.A.C.S.*, 104, 5240–5242 (1982).
Timmons et al., *Inorg. Chem.*, 21, 1525–1529 (1982).
Harris et al., *Inorg. Chem.*, 17, 889–894 (1978).
Price et al., *J. Med. Chem.*, 8, 650–655 (1965) (Abstract Only).

*Primary Examiner*—Helen M. S. Sneed
*Attorney, Agent, or Firm*—J. E. Hasak; Edward M. Corcoran

[57] ABSTRACT

A polydentate binucleating ligand having at least four donor sites selected from N, O and S, complexed with two atoms of the same metal, forms a coordination complex useful in homogeneous catalysis. Most preferably, all the metal cations are Cu cations and the ligand has a meta-xylyl functionality.

8 Claims, No Drawings

BI- OR POLYMETALLIC COORDINATION COMPLEX

BACKGROUND OF THE INVENTION

This invention relates to a coordination complex which is a salt of a cation which consists of at least two metals, one of which is copper I, complexed with a polydentate binucleating ligand. This complex, which reversibly coordinates carbon monoxide, is useful in homogeneous catalysis reactions.

Polydentate amines are known to form stable chelate complexes with a wide variety of metal salts of both main periodic group metals (for example, lithium and sodium as described in U.S. Pat. Nos. 3,734,963 and 3,758,585, respectively) and transition metals including copper (I) as disclosed by C. Floriani et al., *J.A.C.S.*, 103, 185 (1981). In view of their selective complexation of Li and Na salts these amines have a known use in separating alkali metal salts. See, e.g., U.S. Pat. Nos. 3,767,763 and 3,755,533.

Acyclic polydentate amines capable of simultaneously coordinating two metal sites include the bisodium complex described by R. Robson, et al., *J. Inorg. Chem.*, 13, 1301, (1974), wherein the ligand contains a sterically unfavorable phenolic oxygen in the binuclear site, and the bi-copper (I) complex described by J. A. Osborn et al., *J. Chem. Soc. Chem. Comm.*, 498 (1977), wherein the ligand lacks an optimal configuration of ligating functionalities.

Karlin, et al., *J. Chem. Soc. Chem. Comm.*, 881 (1981) describes oxidation of a binuclear Cu (I) species containing a meta-xylyl-binucleating ligand having two tri-dentate ligand donor groups separated by a metaxylene bridge to produce a binuclear Cu (II) complex. In the Cu(I) and Cu(II) complexes the donor groups are unsaturated (pyridyl) groups. The binuclear Cu(I) complex is not characterized in the article, but oxidation thereof to form the Cu(II) complex results in oxidation of the xylene ring. Karlin et al., *J. Coord. Chem.*, 11, 61 (1981) further describes the structure of a Cu(II) complex containing a para-xylyl binucleating ligand. Karlin et al., *J.A.C.S.*, 104, 5240 (1982) describes a three-coordinate binuclear Cu(I) complex containing a meta-xylyl binucleating ligand with pyridyl donor groups and its reaction with air to form the Cu(II) complex. Sorrell et al., *Inorg. Chem.*, 21, 3250 (1982) discloses a three-coordinate binuclear Cu(I) complex containing a meta-xylyl binucleating ligand with pyrazonyl donor groups and its reaction with oxygen to form the Cu(II) complex. Sorrell et al., *J.A.C.S.*, 105, 2054 (1982) discloses another three-coordinate binuclear Cu(I) complex with a meta-xylyl binucleating ligand having pyrazolyl donor groups. J. Timmons and coworkers have described a 2,6-bis(5-(1,4-diazahexyl)pyridine ligand complexed with $Cu^{+2}$ (see *Inorg. Chem.*, 17, 889 (1978) and *Inorg. Chem.*, 21, 1525 (1982)).

Various workers have disclosed binuclear Cu(I) and Cu(I)–Cu(II) complexes of macrocyclic ligands containing 2,6-pyridine, 2,5-furan, and 2,6-phenol fragments. See Drew et al., *J.C.S. Chem. Comm.*, 829 (1980), *J.C.S. Dalton*, 1868 (1981), *J.C.S. Chem. Comm.*, 388 (1981), Gagne et al., *J.A.C.S.*, 99, 8367 (1977) and *J.A.C.S.*, 101, 4571 (1979).

SUMMARY OF THE INVENTION

According to the present invention a novel class of bimetallic or polymetallic complexes containing a polydentate binucleating ligand has been found where the ligand contains at least four donor sites selected from N, O, and S atoms. The ligand provides an environment which can simultaneously complex at least two metal sites and allow sufficient metal site vacancies so as to promote interaction of small molecules and can confer significant stability to the ionic bi- or polymetallic site so that it is less susceptible to dissociation into monometallic species.

Specifically, this invention relates to a coordination complex comprising a salt of a cation consisting of at least two metals, one of which is copper in a +1 oxidation state, complexed with a polydentate binucleating ligand of the formula:

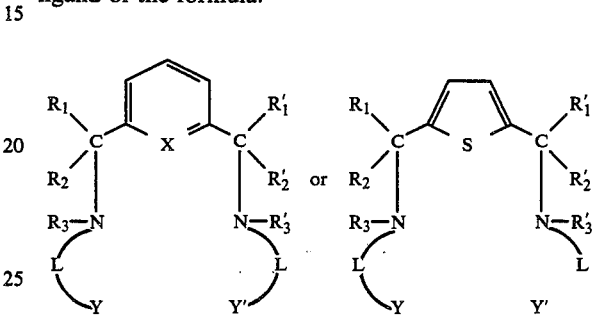

where X is CH or N, Y and Y' are independently selected from the group consisting of —OH, —$NH_2$, —NHR, —$NR_2$ and

where R is a saturated alkyl or saturated alkylene radical, $R_1$, $R_2$, $R_3$, $R'_1$, $R'_2$, and $R'_3$ are independently —H, —$CH_3$ or —$CH_2CH_3$, and L is —$CH_2CH_2$—, —$CH_2CH_2CH_2$—,

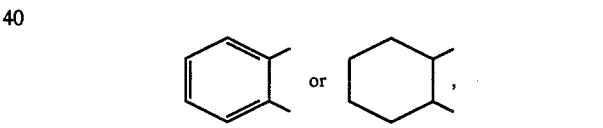

and wherein the metals other than copper in the +1 oxidation state are independently selected from the group consisting of Li, Na, the metals in the first row of the transition metals in the Periodic Table, Ru, Rh, Pd, Ag, Cd, Os, Ir and Pt.

Preferably, in the above formula, X is —CH, $R_1$, $R_2$, $R'_1$ and $R'_2$ are —H, $R_3$ and $R'_3$ are —H or —$CH_3$, L is —$CH_2CH_2$— or —$CH_2CH_2CH_2$—, Y and Y' are —$NH_2$, —$NH(CH_3)$ or —$N(CH_3)_2$, and the other metal(s) in the complex are copper.

Such complexes are useful in homogeneous catalysis reactions due to their ability to absorb CO reversibly, preferably for reactions between CO and $H_2$ under mild conditions of reaction temperature and pressure, such as the synthesis of methanol. In addition, such complexes are useful in gas separations such as in the removal of CO and olefins from gas streams.

DESCRIPTION OF THE PREFERRED EMBODIMENTS

According to the invention herein the coordination complex is a bi- or polymetallic salt of a cation with a net positive charge, which cation is composed of at least two metals, one of which is Cu$^{+1}$, complexed with a polydentate binucleating ligand containing at least four donor atoms for the metals having one of the formulae:

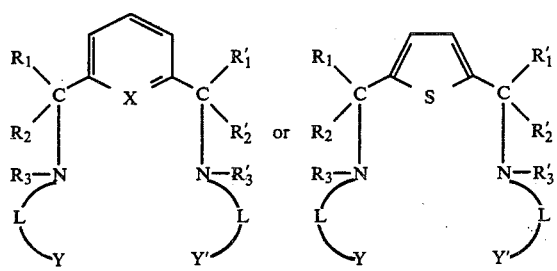

where X is CH or N, Y and Y' are independently selected from the group consisting of —OH, —NH$_2$, —NHR, —NR$_2$ and

where R is saturated alkyl or saturated alkylene radical, R$_1$, R$_2$, R$_3$, R'$_1$, R'$_2$, and R'$_3$ are independently —H, —CH$_3$ or —CH$_2$CH$_3$, and L is —CH$_2$CH$_2$—, CH$_2$—CH$_2$CH$_2$—,

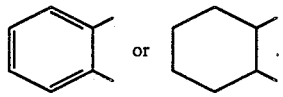

Preferably R is a saturated C$_1$-C$_4$ alkyl or saturated C$_4$-C$_6$ alkylene radical such as a methyl, ethyl, propyl, isopropyl, butyl, tetramethylene, pentamethylene or hexamethylene radical.

The two or more metals, including the copper ion, are complexed with the ligand. Generally, at least one, and more typically two, of the metals are complexed through the donor groups consisting of the two nitrogen (amine) atoms, Y and Y', and S or X if X is N. The metals themselves are generally those which interact or react with amines. One of the metals necessarily is a copper ion in the +1 oxidation state. The other metals which may be present are selected from the group consisting of Li, Na, the first row of the transition metals of the periodic table, i.e., Sc, Ti, V, Cr, Mn, Fe, Co, Ni, Cu and Zn, those transition metals of the second row consisting of Ru, Rh, Pd, Ag and Cd, and those of the third row consisting of Os, Ir and Pt. Preferably these other metals are chosen from Li, Na, Fe, Co, Ni, Cu, Zn, Ru, Rh, Pd, Ag, Cd, Os, Ir and Pt, and more preferably are Fe, Co, Ni, Cu, Pd, and Pt. Most preferably, the complex contains two or three copper metals, all in the +1 oxidation state. If all the copper metals in the complex are in the +2 oxidation state the complex does not coordinate carbon monoxide so that it has little or no catalytic utility and no CO separation capability. Thus, at least one of the metals must be copper in the +1 oxidation state to ensure catalyst or separation utility. The additional metals which may be present in the complex other than copper may be the same or different, and the complex may be prepared by mixing separately or in situ (in the use application) complexes which contain metals other than copper I with complexes containing copper I, e.g., by mixing a Li complex with a Cu complex.

Various methods exist for determining if the metals are complexed with the ligand depending on the physical characteristics of the starting materials and the products. If the metal salt used to prepare the complex is insoluble in the solvent in which the ligand is soluble and the product is insoluble, the increased total weight of precipitate over what would be obtained if only the uncomplexed metal salt were present indicates complexation, and the mixture of solids obtained can be chemically analyzed to determine the amount of metal and carbon in the ligand. If the metal salt is insoluble in the solvent and the product is soluble, complexation is indicated by a decrease in weight of the metal salt due to the complexation of the salt with the ligand. The remaining metal salt may then be analyzed to confirm its composition as an uncomplexed metal salt.

If the metal salt is soluble in the solvent and the product is insoluble, the precipitate can be analyzed to determine its composition as a complex. If both the salt and the product are soluble in the solvent, the complexation can be determined by chemical analysis or by such techniques as NMR spectroscopy, which indicates a change in chemical shifts due to complexation.

The structures, names and abbreviations of representative ligands of this invention are indicated below as examples of suitable species:

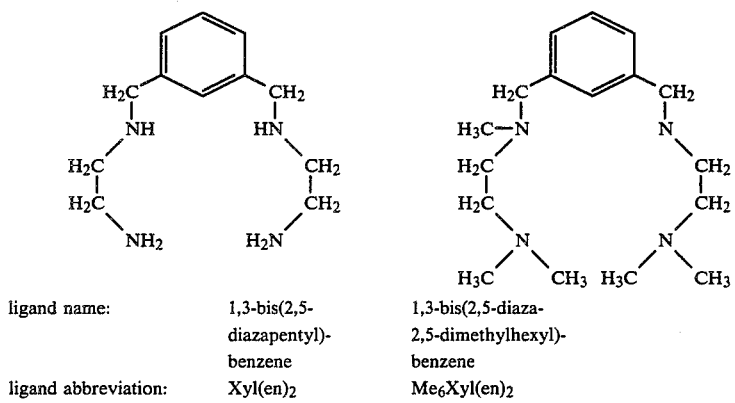

-continued

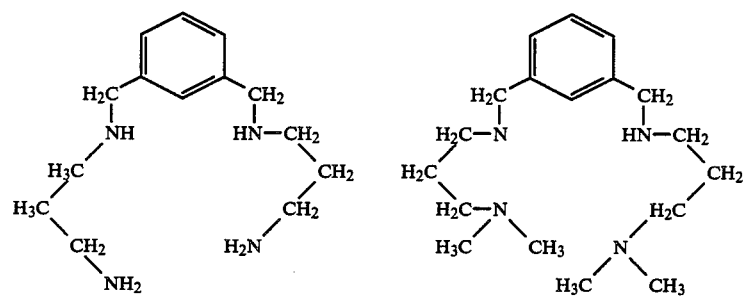

| ligand name: | 1,3-bis(2,6-diaza-hexyl)benzene | 1,3-bis(2,6-diaza-6-methylheptyl)benzene |
|---|---|---|
| ligand abbreviation: | Xyl(tn)$_2$ | Me$_4$Xyl(tn)$_2$ |

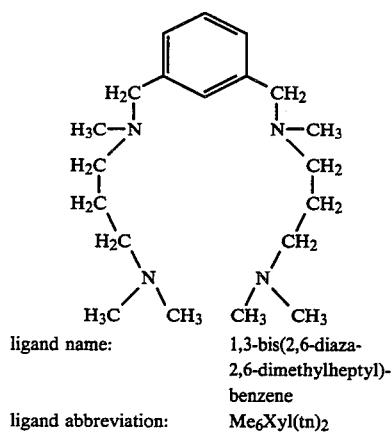
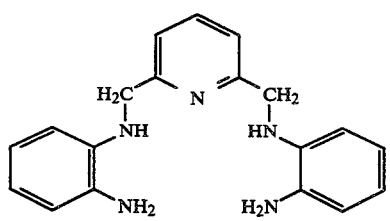

| ligand name: | 1,3-bis(2,6-diaza-2,6-dimethylheptyl)-benzene | 2,6-bis(2-amino-anilinomethyl)-pyridine |
|---|---|---|
| ligand abbreviation: | Me$_6$Xyl(tn)$_2$ | Lut (OPD)$_2$ |

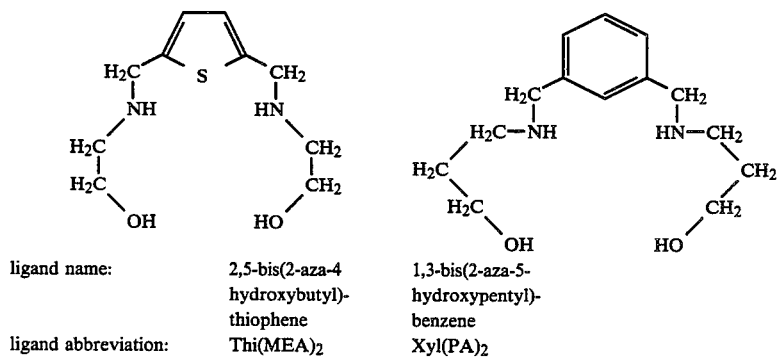

| ligand name: | 2,5-bis(2-aza-4 hydroxybutyl)-thiophene | 1,3-bis(2-aza-5-hydroxypentyl)-benzene |
|---|---|---|
| ligand abbreviation: | Thi(MEA)$_2$ | Xyl(PA)$_2$ |

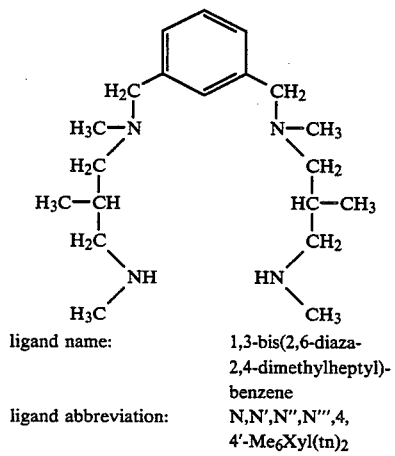
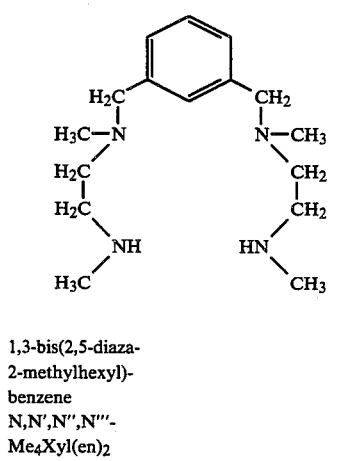

| ligand name: | 1,3-bis(2,6-diaza-2,4-dimethylheptyl)-benzene | 1,3-bis(2,5-diaza-2-methylhexyl)-benzene |
|---|---|---|
| ligand abbreviation: | N,N',N'',N''',4,4'-Me$_6$Xyl(tn)$_2$ | N,N',N'',N'''-Me$_4$Xyl(en)$_2$ |

-continued

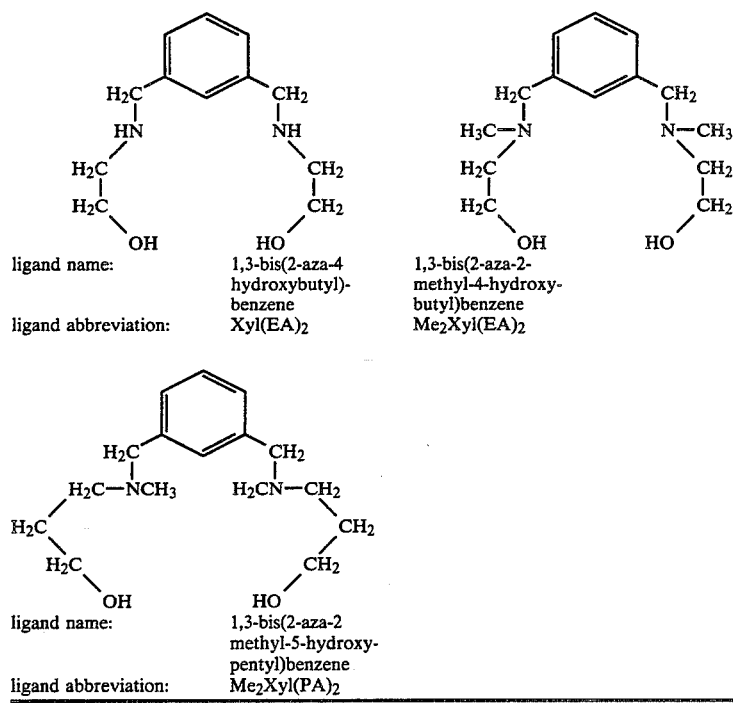

| ligand name: | 1,3-bis(2-aza-4-hydroxybutyl)-benzene | 1,3-bis(2-aza-2-methyl-4-hydroxybutyl)benzene |
|---|---|---|
| ligand abbreviation: | Xyl(EA)$_2$ | Me$_2$Xyl(EA)$_2$ |

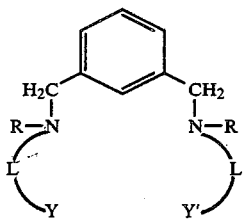

ligand name: 1,3-bis(2-aza-2-methyl-5-hydroxypentyl)benzene
ligand abbreviation: Me$_2$Xyl(PA)$_2$ A more preferred ligand for the complex of this invention has the formula:

where R is hydrogen or a methyl radical, L is —CH$_2$CH$_2$— or —CH$_2$CH$_2$CH$_2$—, and Y and Y' are —NH$_2$, —NH(CH$_3$) or —N(CH$_3$)$_2$. The most preferred cation herein is one in which the metals are all Cu, and the binucleating ligand is 1,3-bis-(2,5-diaza-2,5-dimethylhexyl)benzene (Me$_6$Xyl(en)$_2$) or 1,3-bis(2,6-diaza-2,6-dimethylheptyl)benzene (Me$_6$Xyl(tn)$_2$).

The complex salts of this invention necessarily contain an anion, designated for convenience herein by the letter A, in a molar amount sufficient to neutralize the net positive charge (n) of the cation. Any anion which does not itself react with the gases used for the catalytic reactions may be employed. Examples of suitable such anions are those typically employed to neutralize a cation such as halides (e.g., Cl$^-$, Br$^-$, and I$^-$), NCS$^-$, SO$_4^{-2}$, PF$_6^-$, B(C$_6$H$_5$)$_4^-$, C$_6$H$_5$CO$_2^-$, CH$_3$CO$_2^-$, or mixtures of these anions. In addition, anions such as trifluoromethane sulfonate, catechol dianion, tert-butoxide and the like may be employed. Preferably, the anion is Cl$^-$, NCS$^-$, SO$_4^{-2}$, B(C$_6$H$_5$)$_4^-$, C$_6$H$_5$CO$_2^-$, CH$_3$CO$_2^-$ or a mixture of two or more of these anions. Most preferably at least one of the anions is Cl$^-$, B(C$_6$H$_5$)$_4^-$, C$_6$H$_5$CO$_2^-$ or CH$_3$CO$_2^-$.

The complex of this invention may be coordinated with carbon monoxide by, for example, bubbling a stream of carbon monoxide through a solution of the complex. The complexes herein containing copper (I), which contains d electrons, are found to coordinate carbon monoxide both in the solid state and in solution, indicating that they are useful in the separation of CO from gas streams and in homogeneous catalysis reactions employing carbon monoxide and hydrogen as reactants. In addition, they are useful in gas separation reactions, for example, in the removal of olefins or CO from gas streams.

The ligands in the complex herein may be prepared by any suitable method which will yield the desired compound. If a meta-xylyl ligand with four amino groups is to be prepared, one method is to add dropwise a suitable solution of isophthaldehyde to a solution of the appropriate diamine (such as, e.g., trimethylenediamine or N,N-dimethylethylene diamine). The resultant reaction mixture is refluxed for a sufficient period of time to obtain the results desired, generally from about 3 to 25 hours, depending on the ligand being prepared. After the solution is cooled, a reducing agent such as NaBH$_4$ is added to the solution in more than one portion. The resulting mixture may then be heated at reflux for 0 to 10 hours and thereafter stirred at room temperature for 1 to 3 days. After this period of time the solution may be evaporated to leave a residue which may be extracted with a hot inert solvent such as benzene. The extract thus obtained may be then filtered and evaporated to yield the ligand. Analogous ligands with four amino groups and containing pyridyl or furan moieties are prepared in a similar manner using either 2,6-diacetylpyridine or 2,5-thiophene dicarboxaldehyde, respectively, in place of the isophthaldehyde. The N-permethylated derivatives of certain ligands such as Me$_6$Xyl(en)$_2$ may be derived from their precursors such as Xyl(en)$_2$ by reacting the precursors with formic acid and formaldehyde. Other ligands may not be prepared by this route. For example, Me$_6$Xyl(tn)$_2$ cannot be prepared from Xyl(tn)$_2$ but may be prepared from Me$_4$Xyl(tn)$_2$ by this route.

In an alternative method for preparing the meta-xylyl ligand, a solution of α,α'-dihalo-m-xylene may be added dropwise to a solution of the diamine. After stirring for 1-3 days the solution may be heated at reflux for 3-10 hours, after which a solution of potassium hydroxide or other alkali metal hydroxide is added dropwise to the reaction mixture. The resulting solution may be then heated at reflux for 1-2 hours, evaporated and the residue extracted with an inert solvent such as benzene. Evaporation of the solvent yields the product.

In yet another method for preparing the meta-xylyl ligands, the appropriate amine is added dropwise to a solution of alkyllithium or alkylsodium (e.g., n-butyllithium) in a dry box. To this solution is added a solution of isophthaloyl dihalide, e.g., dichloride, in an appropriate amount. A solid consisting of a mixture of amine and lithium halide or sodium halide is filtered from the resulting reaction mixture. This solid is dissolved in an appropriate inert solvent and added dropwise to a suspension of a reducing agent such LiAlH$_4$ in diethylether. After the addition the reaction mixture may be stirred for up to 3 days at room temperature and then stirred for up to 2 days at reflux temperature. A solution of ethylacetate is then added dropwise to the reaction mixture after it is cooled and the resulting mixture is heated at reflux for up to 2 days. Water is then added dropwise to the mixture followed by heating at reflux for 6 hours. The organic phase may then be separated, dried with MgSO$_4$ and concentrated in vacuo to yield the desired ligand.

The complex itself may be prepared from the ligand, usually in an inert atmosphere such as Ar, CO, N$_2$ or H$_2$, by mixing in an inert solvent the appropriate ligand with a salt containing the metal cation(s) and anion(s) desired in the final complex, such as, e.g., LiNCS, ZNSO$_4$, CuI, CuCl, etc., with the amount of salt employed being at least twice the molar equivalents of the ligand employed. Depending on the solubility of the salt, the total amount of salt required may be added initially, or a portion of the salt may be added, with the remainder being added when the first portion is sufficiently dissolved. The mixture is generally stirred under a nitrogen atmosphere for at least one day to effect dissolution of the components, whereupon the reaction mixture is filtered. Depending on the complex being prepared, the product will be either in the filtrate or in the solid which is filtered from the solution.

A carbon-monoxide-coordinated complex may be prepared from the complex thus obtained by bubbling (or sparging) carbon monoxide gas through the solution of the reagents while optionally exchanging the anion of the metal by slowly adding a salt having a compensating anion such as thallium benzoate to the solution. After stirring the solution at room temperature for one hour it is filtered to remove the anion-exchanged salt, such as thallium iodide if a metal iodide is employed as reactant. The filtrate is then returned to a CO atmosphere and a solution of a salt with a compensating anion such as sodium tetraphenylborate is added slowly. After stirring under CO gas for up to 3 hours the mixture is filtered and the filtrate is evaporated to yield the product.

The following examples are provided to illustrate but not limit the invention. In these examples all parts and percentages are by weight and all temperatures are in degrees Centigrade unless otherwise indicated. All organic and inorganic reagents used to prepare the ligands and complexes were commercially available.

EXAMPLE 1

Preparation of Me$_6$Xyl(en)$_2$ Ligand

In a dry box 37.5 mL (60 mmol) of 1.6M n-butyllithium in hexane was charged to a 125 mL flask and 6.0 g (60 mmol) of N,N,N'-trimethylethylene diamine was added dropwise giving an exothermic reaction. To the resulting hazy reaction mixture was added dropwise a solution containing 6.09 g (30 mmol) of isophthaloyl dichloride in diethylether. The exothermic reaction was accompanied by precipitation of about 12 g of solid (96% of theory for a mixture of the diamide product plus 2 LiCl) which was isolated by filtration. No material was left in the filtrate following vacuum stripping. A 9.29 g portion of the solid was dissolved in 85 mL of 1,3-dioxolane and was added dropwise to a suspension of LiAlH$_4$ (1.7 g, 45 mmol) in 300 mL of diethylether. During this addition the brown solution became light yellow. The reaction mixture was stirred for 2 days at ambient temperature and then for one day at reflux temperature. To the cooled reaction mixture was added dropwise a solution of ethylacetate (5 mL) in diethylether (10 mL), and the resulting mixture was heated at reflux temperature for one day. Water (5 mL) was then added dropwise followed by heating at reflux temperature for 6 hours. The organic phase was then separated, dried with MgSO$_4$, and concentrated in vacuo to 5.6 g of a pale yellow liquid which was characterized as the title compound (yield 82%).

Analysis: Calc. for C$_{18}$H$_{34}$N$_4$, molecular weight (MW) 306.496; C 70.54, H 11.18, N 18.28%. Found: C 68.98, H 10.44, N 16.04%.

NMR spectrum (C$_6$D$_6$ vs. interval tetramethylsilane (TMS): δ 7.39, 7.19 (broad apparent singlets, aromatic protons, 3.8H); δ 3.42, 2.42, and 2.09 (broad apparent singlets, aliphatic protons, 30H).

This example shows that acyclic binucleating ligands having tertiary amine functions can be prepared conveniently and in good yields.

EXAMPLE 2

Alternative Preparation of Me$_6$Xyl(en)$_2$ Ligand

To 5.03 g (50 mmol) N,N,N'-trimethylethylenediamine in 30 mL of pentane was added dropwise a solution of butyllithium in hexane (3.5 mL, 1.5M) which had been further diluted with about 40 mL pentane. After this addition was complete, the reaction mixture was warmed to reflux for 15 min., and then was cooled to room temperature. A solution of α,α'-dichloro-m-xylene (4.38 g, 25 mmol) in 75 mL dry diethyl ether was added dropwise and the resulting slurry was allowed to stir overnight at room temperature. Filtration afforded 2.03 g of white powder (theory for LiCl is 2.12 g). The filtrate was evaporated to give 7.49 g (98%) of the desired tetraamine. The latter was vacuum distilled through a short path still (boiling point about 200°-220° C./0.6 Torr). An $^1$H NMR spectrum of the distilled product (C$_6$D$_6$-TMS) was identical to that reported in Example 1.

Analysis: Calc. for C$_{18}$H$_{34}$N$_4$, MW 306.502: C 70.54%, H 11.18%, N 18.28%. Found: C 70.93%, H 11.28%, N 18.04%.

This example shows that binucleating ligands can be prepared in excellent yields by a single step synthesis.

EXAMPLE 3

Preparation of N,N',N",N'"—Me4Xyl(en)2 Ligand

To an excess of N,N'-dimethylethylenediamine (17.63 g, 200 mmol) in 100 mL absolute ethanol was added dropwise over 2 hours a solution of α,α'-dichloro-m-xylene (8.75 g, 50 mmol) in 100 mL absolute ethanol. The resulting clear yellow solution was heated at reflux for 7 hours and then was cooled to room temperature, and a solution of KOH pellets (6.6 g, 100 mmol) in 75 mL methanol was added. After warming the resulting slurry at reflux for about 4 hours, the by-product KCl (7.26 g, 97%) was recovered by filtration, and the filtrate was concentrated to give 10.63 g of the desired tetraamine.

Analysis: Calc. for $C_{16}H_{30}N_4$, MW 278.448: C 69.02%, H 10.86%, N 20.12%. Found: C 68.38%, H 9.94%, N 18.29%.

NMR Spectrum (Dimethylsulfoxide (DMSO)-$d_6$-TMS): δ 7.25 (broad apparent singlet, aromatic protons 4H), δ 3.50 (singlet, benzylic protons, 4H), δ 2.52 (multiplet, $NCH_2$, 8H), and δ 2.4, 2.27 (singlets, $NCH_3$, 12H).

EXAMPLE 4

Preparation of Xyl(EA)2 Ligand

To a solution of ethanolamine (60 mL, 1 mol) in 400 mL absolute ethanol was added dropwise over 3 hours a solution of α,α'-dichloro-m-xylene (17.5 g, 0.1 mol) in 200 mL ethanol. After stirring overnight this solution was heated at reflux for 8 hours. A solution of KOH (12.3 g, 0.22 mol) in 100 mL methanol was then added dropwise over one hour and after stirring for 2 days, 14.6 g KCl (theory 14.9 g) was recovered by filtration. The filtrate was evaporated to a clear oily liquid and after vacuum treatment (1 Torr, 5 hr.) a constant weight was achieved (21.6 g, 96% yield).

NMR Spectrum ($D_2O$-TSP): δ 7.22 (broad singlet, aromatic protons, 4H); δ 4.96 (sharp singlet, protons derived from NH and OH functionalities, 4H); δ 3.78 (multiplet, benzylic protons and $-CH_2O$, 8H); and δ 2.74 (triplet J 5 Hz, $-CH_2N$, 4H).

Analysis: Calc. for $C_{12}H_{20}N_2O_2$, MW 224.308: C 64.26%, H 8.99%, N 12.49%. Found: C 65.12%, H 8.82%, N 12.22%.

This example shows the preparation of a ligand containing oxygen and secondary amine functionalities.

EXAMPLE 5

Preparation of Me2Xyl(EA)2 Ligand

To 150 mL of aqueous formic acid was added 14.02 g (62.5 mmol) of 1,3-bis(2-aza-4-hydroxybutyl)benzene followed dropwise by 80 mL of 37% aqueous formaldehyde. After heating on a steam bath for 24 hr., 50 mL concentrated HCl was added and the mixture was vacuum stripped to a sludge. Water (40 mL) was added and the evaporation was repeated. With ice bath cooling the resulting residue was treated carefully with 120 mL of 50% NaOH solution and then was extracted with 4×150 mL portions of ether. The combined extracts were filtered and concentrated to a viscous oil. This oil was maintained at 0.1 Torr for six hours to give 14.7 g (93%) of the title compound.

Analysis: Calc. for $C_{14}H_{24}N_2O_2$, MW 252.360: C 66.63%, H 9.59%, N 11.10%. Found: C 67.57%, H 9.59%, N 10.29%

NMR ($C_6D_6$-TMS): δ 7.20, 7.31 (broad singlets, aromatic protons, 4H); δ 4.6–4.8 (impurity 0.8H); δ 4.16 (singlet, hydroxyl protons, 2H); δ 3.65 (triplet J 5.5 Hz, $-CH_2O-$, 4H); δ 3.45 (singlet, benzylic protons, 4H); δ 2.48 (triplet, $-CH_2N-$, 4H); and δ 2.14 (singlet, $-NCH_3$, 6H).

This example shows the preparation of a ligand containing tertiary amino and alcohol functionalities.

EXAMPLE 6

Preparation of Xyl(PA)2 Ligand

To a solution of 3-amino-1-propanol (75 g, 1 mol) in 300 mL absolute ethanol was added dropwise over 3 hours a solution of α,α'-dichloro-m-xylene (17.5 g, 0.1 mol) in 200 mL ethanol. After warming at reflux for 8 hours, a solution of 85% KOH pellets (12.3 g, 0.2 mol) in 100 mL methanol was added and 14.7 g KCl was recovered by filtration. The filtrate was concentrated and the oily residue was dissolved in benzene containing a trace of ethanol. This solution was filtered and the filtrate was evaporated to give 25.0 g (quantitative) of the title ligand as a pale yellow viscous oil.

Analysis: Calc. for $C_{14}H_{24}N_2O_2$, MW 252.362: C 66.63%, H 9.59%, N 11.10%, O 12.68%. Found: C 65.47%, H 9.14%, N 10.80%

NMR Spectrum ($D_2O$-TSP): δ 7.29 (broad apparent singlet, aromatic protons, 4H); δ 4.96 (singlet, protons derived from NH and OH functionalities, 4H); δ 3.69 (superimposed singlet and triplet, benzylic protons and $OCH_2$, respectively, 8H); δ 2.67 (triplet J 6.5 Hz, $NCH_2$, 4H); and δ 1.78 (partially resolved quintet J 6.5 Hz, $C-CH_2-C$, 4H).

This represents another example of a ligand containing secondary amino and alcohol coordinating functionalities.

EXAMPLE 7

Preparation of Me2Xyl(PA)2 Ligand 1,3-Bis(2-aza-5-hydroxypentyl)benzene (6.31 g, 25 mmol) was added to 60 mL aqueous formic acid followed dropwise over 2 hours by 80 mL 37% aqueous formaldehyde with steam bath heating. Heating was discontinued after 2 days whereupon conc. HCl (20 mL) was added with stirring. The resulting solution was concentrated on a vacuum rotary evaporator, water (10 mL) was added, and concentration was repeated. The residue obtained was treated cautiously (ice bath cooling) with 50 ml 50% aqueous NaOH solution and then was extracted with 3×125 mL portions of diethyl ether. The combined extracts were filtered and evaporated to a viscous oil. Exposure of this oil to 0.1 Torr for 4 hours afforded 5.2 g (74%) of the title amino alcohol.

Analysis: Calc. for $C_{16}H_{28}N_2O_2$, MW 280.416: C 68.53%, H 10.07%, N 9.99%. Found: C 68.85%, H 9.70%, N 9.35%.

NMR Spectrum ($C_6D_6$-TMS): δ 7.39, 7.20 (broad singlets, aromatic protons, 4H); δ 4.6–4.75 (multiplet, hydroxyl protons, 2H); δ 3.70 (triplet J 6 Hz, $-CH_2O$, 4H); δ 3.40 (singlet, benzylic protons, 4H); δ 2.46 (triplet J 6 Hz, $-CH_2N$, 4H); δ 2.09 (singlet, $NCH_3$, 6H); and δ 1.69 (multiplet, $C-CH_2-C$, 4H).

This example shows the preparation of a ligand containing tertiary amino and alcohol functionalities.

EXAMPLE 8

Preparation of Xyl(en)2 Ligand

Isophthaldehyde (13.4 g, 0.1 mol) in 100 mL of absolute methanol was added to a solution of ethylene diamine (104 mL, about 1.56 mol) in 1.2 L methanol. This solution was heated at reflux for 4 hours whereupon it was allowed to cool. Over a period of 30 minutes, a solution of NaBH$_4$ (15 g, 400 mmol) in 150 mL of methanol was added in three portions. The resulting mixture was heated at reflux for 6 hours and then was stirred overnight at room temperature. The residue obtained on evaporation was extracted with ca. 0.4 L of hot benzene. The clear benzene extract was filtered and evaporated to give 15.48 g of the title compound as a yellow oil.

Analysis: Calc. for C$_{12}$H$_{22}$N$_4$, MW 222.33; C 64.83, H 9.97, N 25.20%. Found: C 65.05, H 9.81, N 25.27%.

NMR Spectrum (D$_2$O-sodium beta-trimethylsilylpropionate (TSP)): $\delta$ 7.33 (singlet, aromatic protons, 4H); $\delta$ 4.83 (singlet, protons derived from amine functions, 6H); $\delta$ 3.74 (singlet, benzylic protons, 4H); and $\delta$ 2.69 (apparent triplet, NCH$_2$, 8H).

NMR Spectrum (C$_6$D$_6$-TMS): $\delta$ 7.40, 7.25 (singlets, aromatic protons, 4H); $\delta$ 3.70 (singlet, benzylic protons, 4H); $\delta$ 3.59 (apparant singlet, NCH$_2$, 8H); and $\delta$ 1.25 (broad singlet, NH$_2$, 6H).

This example demonstrates the straightforward preparation of another binucleating ligand containing primary and secondary amine functionalities. Analogous pyridyl and furyl ligands may be prepared using this technique by substituting for the isophthaldehyde either 2,6-diacetylpyridine or 2,5-thiophene dicarboxaldehyde, respectively.

EXAMPLE 9

Preparation of Xyl(tn)$_2$ Ligand

To 120 mL (about 1.44 mol) of trimethylenediamine in 750 mL ethanol was added dropwise over about 2 hours a solution of $\alpha,\alpha'$-dibromo-m-xylene (26.4 g 0.1 mol) in 500 mL ethanol. After stirring overnight the solution contained a white precipitate which dissolved on warming. The clear solution was heated at reflux for 6 hours and then a solution of KOH (12.3 g, 0.22 mol) in 100 mL methanol was added dropwise. The cloudy solution obtained was heated at reflux temperature for one hour and evaporated, and then the resulting residue was extracted with benzene. Evaporation of the benzene extracts left the title compound as a yellow oil (18.2 g, 73% yield).

Analysis: Calc. for C$_{14}$H$_{26}$N$_4$, MW 250.394; C 67.16, H 10.47, N 22.38%. Found: C 67.74%, H 10.62%, N 22.35%.

NMR Spectrum (C$_6$D$_6$-TMS): $\delta$ 7.42, 7.25 (apparent singlets, aromatic protons, 4H); $\delta$ 3.67 (singlet, benzylic protons, 4H); $\delta$ 2.60 (triplet of doublets, NCH$_2$, 8H); $\delta$ 1.47 (quintet J 6.7 Hz, C—CH$_2$—C, 4H); and $\delta$ 0.97 (singlet, amine protons, 6H).

NMR Spectrum (D$_2$O-TSP): $\delta$ 7.33 (broad singlet, aromatic protons, 4H); $\delta$ 4.85 (singlet, protons derived from amine functions, 6H); $\delta$ 3.73 (broad singlet, benzylic protons, 4H); $\delta$ 2.60 (multiplet, NCH$_2$, 8H); and $\delta$ 1.64 (quintet J ca. 6 Hz, C—CH$_2$—C, 4H).

This example demonstrates the synthesis of another binucleating ligand containing both primary and secondary amine functions.

EXAMPLE 10

Preparation of Me$_4$Xyl(tn)$_2$ Ligand

To a solution of 20.4 g (0.2 mol) of 3-dimethylaminopropylamine in 400 mL methanol was added dropwise over 2 hours a solution of isophthalaldehyde (13.4 g, 0.1 mol) in 200 mL methanol. The resulting clear yellow solution was heated at reflux temperature for 18 hours. After cooling the solution to 0° C., three 5 g, (0.13 mol) portions of NaBH$_4$ in 50 mL methanol were added at 30 min. intervals. After stirring at room temperature for 2 days, the solution was vacuum stripped to a clear, yellow gel-like residue. This residue was extracted with hot benzene and the extracts were concentrated in vacuo to give 26.8 g (88%) of the title compound as a clear liquid.

Analysis: Calc. for C$_{18}$H$_{34}$N$_4$, MW 306.502; C 70.54, H 11.18, N 18.28%. Found: C 69.98, H 11.02, N 18.13%.

NMR Spectrum (dimethylsulfoxide-d$_6$-TMS): $\delta$ 7.22, 7.12 (broad singlets, aromatic protons, 4H); $\delta$ 3.64 (singlet, benzylic protons, 4H); $\delta$ 2.54, 2.23 (apparent triplets, NCH$_2$, 8H); $\delta$ 2.11 (singlet, CH$_3$, 12H); $\delta$ 2.0–2.8 (multiplet, amine protons, 2H); and $\delta$ 1.53 (quintet J=6.6 Hz, C—CH$_2$—C, 4H).

NMR Spectrum (D$_2$O-TSP): $\delta$ 7.3 (broad overlapping singlets, aromatic protons, 4H); $\delta$ 4.95 (singlet, protons derived from amine functions, 2H); $\delta$ 3.75 (broad singlet, benzylic protons, 4H); $\delta$ 2.3–2.8 (multiplets, NCH$_2$, 8H); $\delta$ 2.21 (singlet, CH$_3$, 12H); and $\delta$ 1.5–2.0 (multiplet, C—CH$_2$—C, 4H).

This example demonstrates the preparation of another binucleating ligand which contains secondary and tertiary amine functionalities.

EXAMPLE 11

Preparation of Me$_6$Xyl(tn)$_2$ Ligand

Reaction of Me$_4$Xyl(tn)$_2$ obtained from Example 10 with formic acid and formaldehyde afforded after workup the title compound, which is the N-permethylated derivative (81% yield).

Analysis: Calc. for C$_{20}$H$_{38}$N$_4$, MW 334.556; C 71.80, H 11.45, N 16.75%. Found: C 71.20, H 11.34, N 16.47%.

NMR Spectrum (C$_6$D$_6$-TMS): $\delta$ 7.42, 7.25 (singlets, aromatic protons, 4H); $\delta$ 3.43 (singlet benzylic protons, 4H); $\delta$ 2.49 and 2.13 (overlapping apparent triplet J 7 Hz and singlet, NCH$_2$ and CH$_3$, respectively, 26H); and $\delta$ 1.83–1.42 (multiplet, C—CH$_2$—C, 4H).

This example demonstrates another synthetic approach to acyclic binucleating ligands which contain tertiary amine functionalities.

EXAMPLE 12

Preparation of Ligand.Cu$_2$Cl$_2$ Complexes

Two equivalents of CuCl were suspended in THF containing one equivalent of the dissolved, polydentate ligand indicated in Table I. Depending on the exact nature of the ligand structure, 2:1 CuCl:ligand complexes were isolated either as precipitates (complexes with limited solubility), or upon evaporation of the resulting solutions (soluble complexes). The products, characterized by elemental analysis, are tabulated in Table I.

TABLE I

Analysis of Ligand · Cu$_2$Cl$_2$ Complexes

| Ligand Abbrev. | THF Solubility | Percentages Calc. (Found) | | | | |
|---|---|---|---|---|---|---|
| | | C | H | N | Cl | Cu |
| Me$_6$Xyl(en)$_2$ | Soluble | 42.85 | 6.79 | 11.12 | 14.05 | 25.19 |
| | | (42.95) | (6.77) | (11.21) | (13.87) | (25.96) |
| Me$_6$Xyl(tn)$_2$ | Soluble | 45.11 | 7.20 | 10.52 | 13.31 | 23.86 |
| | | (46.69) | (7.57) | (10.25) | (11.79) | (25.48) |
| N,N',N'',N''',4,4'-Me$_6$Xyl(tn)$_2$ | Soluble | 45.11 | 7.20 | 10.52 | 13.31 | 23.86 |
| | | (45.58) | (7.19) | (9.08) | (11.30) | (*) |
| N,N',N'',N'''-Me$_4$Xyl(en)$_2$ | Partially Soluble | 40.34 | 6.35 | 11.76 | 14.88 | 26.67 |
| | | (45.56) | (6.80) | (11.69) | (11.61) | (*) |
| N,N,N'',N'''-Me$_4$Xyl(tn)$_2$ | Precipitate | 42.86 | 6.79 | 11.11 | 14.01 | 25.23 |
| | | (41.71) | (6.39) | (11.53) | (12.26) | (*) |
| Xyl(en)$_2$ | Precipitate | 34.29 | 5.28 | 13.33 | 16.87 | 30.23 |
| | | (36.31) | (5.55) | (11.96) | (14.65) | (*) |
| Xyl(tn)$_2$ | Precipitate | 37.50 | 5.84 | 12.50 | 15.81 | 28.35 |
| | | (37.85) | (5.93) | (12.24) | (16.85) | (*) |

*Not determined experimentally but are expected to be close to calculated values.

The foregoing experiments demonstrate that a wide variety of the binucleating ligands herein form stable complexes with simple salts such as CuCl.

EXAMPLE 13

Anion Metathesis Reactions with CuCl Complexes

THF solutions of 2:1 complexes of CuCl:Ligand (where the ligand was either Me$_6$Xyl(en)$_2$ or Me$_6$Xyl(tn)$_2$) obtained from Example 12 were stirred with two equivalents of either thallium benzoate or thallium acetate and the less soluble thallium chloride formed by anion metathesis was allowed to precipitate. The resulting slurries were sparged with CO and were filtered prior to analysis by IR spectrophotometry. The results of these analyses are tabulated below in Table II and demonstrate the capability of the copper complexes herein to coordinate CO in solution.

TABLE II

Infra-Red Analysis of CO Bands in THF Solutions of L:Cu$_2$A$_2$ Complexes

| Ligand (L) | Anion (A) | Y cm$^{-1}$ (relative intensity)* | |
|---|---|---|---|
| Me$_6$Xyl(tn)$_2$ | C$_6$H$_5$CO$_2$— | 2058 s | 1920 s |
| Me$_6$Xyl(tn)$_2$ | CH$_3$CO$_2$— | 2050 m | 1925 m |
| Me$_6$Xyl(en)$_2$ | C$_6$H$_5$CO$_2$— | 2058 vs | 1925 w |
| Me$_6$Xyl(en)$_2$ | CH$_3$CO$_2$— | 2060 s | |

*vs = very strong, s = strong, m = medium, w = weak

Other metathesis reactions with CuCl complexes which occurred were those using thallium trifluoromethane sulfonate, disodium catecholate and sodium tert-butoxide as the reactants.

EXAMPLE 14

Preparation of Me$_6$Xyl(en)$_2$·Cu$_2$(C$_6$H$_5$CO$_2$)·(B(C$_6$H$_5$)$_4$)(CO)$_x$
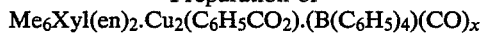

Under an atmosphere of dry N$_2$ were combined 3.07 g (10 mmol) of Me$_6$Xyl(en)$_2$, obtained from Example 1, 100 mL of dioxolane, and 3.8 g (20 mmol) of CuI to give a clear solution. By means of a gas dispersion tube, a stream of CO was bubbled through this solution while 6.51 g (20 mmol) of thallium benzoate was slowly added in portions through a solids transfer tube. After stirring at room temperature for one hour, the solution was filtered and thallium iodide (6.75 g, 99%) was recovered. The filtrate was returned to a CO atmosphere and infrared (IR) analysis showed $\nu_{CO}$ bands at 1950 and 2070 cm$^{-1}$. A solution of sodium tetraphenylborate (3.42 g, 10 mmol) in 40 mL dioxolane was then added over 15 minutes resulting in an apparent increase in the viscosity of the solution and a change in color from green to yellow. After stirring under CO gas for 2 hours, the mixture was suction filtered (in the dry box) to give 1.25 g of a solid (theory for sodium benzoate 1.44 g) and a light green filtrate ($\nu_{CO}$ bands at 1950 and 2040 cm$^{-1}$). Evaporation of the filtrate afforded 8.39 g of a pale green solid. An IR spectrum of this solid in dioxolane reproduced the $\nu_{CO}$ bands at 1950 and 2040 cm$^{-1}$ seen prior to vacuum evaporation.

This example shows that binuclear Cu(I) complexes with the Me$_6$Xyl(en)$_2$ ligand coordinate CO both in the solid state and in solution.

EXAMPLE 15

Air Oxidation of Me$_6$Xyl(en)$_2$Cu$_2$Cl$_2$

To a solution of distilled Me$_6$Xyl(en)$_2$(0.61 g, 2 mmol) in 50 mL dry THF was added cuprous chloride (0.40 g, 4 mmol). After stirring overnight, the clear orange-brown solution was filtered and concentrated to give a quantitative yield of Me$_6$Xyl(en)$_2$Cu$_2$Cl$_2$. This product was transferred to a 30 mL clear glass bottle containing a tetrafluoroethylene-coated stirring bar. After sealing with a rubber septum, the bottle was partially evacuated via syringe while about 25 mL of dry, degassed methanol (stored over 4A molecular sieves and sparged for 30 min. with dry N$_2$) was introduced by means of a cannula.

Under a nitrogen atmosphere, the clear yellow-brown solution remained unchanged after stirring overnight. Exposure of this solution to air resulted in an immediate color change to dark green. (Independent gas absorption experiments revealed an O$_2$:di-copper complex reaction stochiometry of 0.95±0.09:1.) Isolation of the air oxidation product by solvent evaporation yielded dark green crystals, mp 89°-93° C.

Analysis: Calc. for C$_{18}$H$_{34}$N$_4$Cu$_2$Cl$_2$(OH)$_2$: C 40.15%, H 6.74%, N 10.40%, Cl 13.17%, Cu 23.60%. Found: C 40.54%, H 6.67%, N 9.95%, Cl 13.83%, Cu 24.07%;

IR (mull) shows a broad OH absorption between 3100-3650 cm$^{-1}$).

After 30 min. contact with air, the dark green solution was filtered (0.03 g of insoluble residue). The filtrate was slowly added by pipet to a solution of Na$_2$S·9H$_2$O (1.2 g, 5 mmol) in 100 mL distilled water. After stirring for 3 hr., filtration afforded 0.39 g of a black solid (theoretical yield for CuS, 0.382 g).

The filtrate was acidified with dilute HCl to pH 3 and then was evaporated. This process was repeated two times until H$_2$S could no longer be detected in the evaporation residue. To this residue was added benzene (50 mL), 50% NaOH solution (15 drops) and 15 mL distilled water. Following this exothermic neutralization, the mixture was heated to boiling and the organic layer was recovered. The aqueous portion was extracted with fresh benzene and the combined benzene extract was evaporated. The residue was maintained at 0.01 Torr at room temperature until a constant weight was achieved. $^1$H and $^{13}$C nmr examination of the clear, oily residue showed it to be identical to the starting ligand (there was no evidence of aromatic ring hydroxylation which would have resulted in a significant downfield shift for one of the aromatic carbons). Ligand recovery was 90%.

This experiment demonstrates that appropriately substituted binucleating ligands do not undergo hydroxylation of their aromatic component on exposure of their di-copper (I) complexes to air in methanol. This contrasts with oxidation of a Cu(I) ligand complex reported by Karlin et al., *J. Chem. Soc. Chem. Comm.*, 881 (1981), which results in oxidation of the xylene ring.

EXAMPLE 16

Preparation of, and Coordination of CO by, Me$_6$Xyl(en)$_2$Cu$_3$Cl$_3$ Complex In a first experiment cuprous chloride (1.0 g, 10 mmol) in 50 mL THF was stirred for 16 hours at 25° C. under a nitrogen atmosphere. Upon filtration the CuCl was recovered quantitatively, indicating that CuCl is virtually insoluble in THF.

In a separate experiment, to a solution of Me$_6$Xyl(en)$_2$ (1.54 g, 5 mmol) in 100 mL THF was added an excess of CuCl (2.98 g, 30 mmol). After stirring overnight, filtration afforded 1.51 g (about 15 mmol) CuCl, indicating coordination or complexation of the Cu cations to the ligand. Evaporation of the filtrate gave 3.0 g of a solid product which represented a theoretical yield of Me$_6$Xyl(en)$_2$Cu$_3$Cl$_3$.

Analysis: Calc. for C$_{18}$H$_{34}$N$_4$Cu$_3$Cl$_3$, MW 603.493: C 35.83%; H 5.68%; N 9.28%; Cu 31.59%; Cl 17.62%. Found: C 38.46%; H 6.03%, N 8.99%, Cu 29.26%, Cl 17.31%.

A THF solution containing a 3:1 mole ratio of the CuCl/Me$_6$Xyl(en)$_2$ so prepared was exposed to a stream of CO at 25° C. IR analysis of the resulting solution revealed a strong CO absorption at 2060 cm$^{-1}$ indicative of a CO ligand bound to Cu$^+$.

This example demonstrates the complexation capacity of Me$_6$Xyl(en)$_2$ for cuprous chloride in THF and the coordination of CO by the resulting complex.

EXAMPLE 17

Preparation of Me$_6$Xyl(en)$_2$Li$_2$Br$_2$ Complex

Under an N$_2$ atmosphere, a 6.13 g (about 20 mmol) sample of crude Me$_6$Xyl(en)$_2$ (reddish-brown oil) prepared by Example 2 was dissolved in 150 mL toluene and 3.47 g (40 mmol) LiBr was added over about one hour in portions. Stirring was continued overnight. Filtration through a medium porosity sintered glass funnel recovered 1.9 g of a light orange powder. Upon concentrating and cooling, the filtrate afforded 2.8 g of crystals which were washed with pentane, dried, and analyzed (mp 237°–40° C.). Continued evaporation of the filtrate yielded 3.93 g of orange solid.

Analysis: Calc. for C$_{18}$H$_{34}$N$_4$Li$_2$Br$_2$, MW 480.19: C 45.02%, H 7.14%, N 11.67%, Li 2.89%, Br 33.28%. Found: C 45.68%, H 7.71%, N 12.16%, Li 2.70%, Br 31.93%.

NMR(C$_6$D$_6$-TMS): δ 9.4 (apparent trace impurity); δ 6.8–7.25 (multiplet, aromatic protons, 4H); δ 2–4 (broad unresolved resonance, benzylic protons, about 4H); δ 1.92 and 2.30 (singlets, NCH$_3$, overlapping a broad unresolved resonance, NCH$_2$, total about 26H).

This example shows the binucleating capability of a polyamine ligand herein.

A similar experiment employing LiCl rather than LiBr did not result in a complex, indicating that a mixture of LiCl and LiBr could be separated by exposure of the mixture to a solution of the ligand, which will complex the LiBr but not the LiCl.

EXAMPLE 18

Preparation of Me$_6$Xyl(en)$_2$.(LiNCS)$_2$ Complex 1,3-Bis-(2,5-diaza-2,5-dimethylhexyl)benzene (Me$_6$Xyl(en)$_2$) (2.8 g, ca. 9.15 mmol) obtained from Example 1 and LiNCS (1.2 g, 18.3 mmol) were combined in about 20 mL of toluene and the mixture was stirred under N$_2$ gas for about one day. The reaction mixture was filtered and the clear filtrate was evaporated to give a pale tan solid. Washing this with pentane afforded 2.6 g (70%) of the title complex, with melting point 197°–200° C.

Infrared (IR) Spectrum: $\nu_{NC}$ 2050 cm$^{-1}$ (strong, sharp).

NMR Spectrum (C$_6$D$_6$ vs. internal TMS): δ 8.10 (broad singlet, aromatic H on C$_2$, 1H); δ 7.14 (apparent 1:1:1 triplet, aromatic H on C$_5$, 1H); δ 6.95 and 6.82 (broad apparent singlets, aromatic H's on C$_4$ and C$_6$, 2H); and δ 3.21, 2.20, 2.02, and 1.77 (singlets and broad apparent singlets, aliphatic protons, 30H).

Analysis: Calc. for C$_{18}$H$_{34}$N$_4$.(LiNCS)$_2$, MW 436.502; C 55.03, H 7.79, N 19.24, S 14.69, and Li 3.21%. Found: C 55.06%, H 7.96%, N 19.13%, S 14.61%, and Li 3.10%.

This example shows that acyclic binucleating ligands form stable complexes with two equivalents of metal salts. The complex herein may be mixed with a complex containing Cu(I) so as to obtain a complex useful in homogeneous catalysis.

EXAMPLE 19

Preparation of Me$_6$Xyl(en)$_2$.(ZnSO$_4$)$_2$ Complex

To a solution of 1,3-bis-(2,5-diaza-2,5-dimethylhexyl)-benzene (Me$_6$Xyl(en)$_2$) (0.92 g, 3 mmol) obtained from Example 1 in 45 ml methanol was added one equivalent of ZnSO$_4$. ~7H$_2$O (0.86 g, 3 mmol). After 3 hours of stirring most of the zinc salt had dissolved to give a hazy solution. The remainder of the ZnSO$_4$. ~7H$_2$O (0.86 g, 3 mmol) was then added along with 45 ml methanol. The slurry obtained was stirred overnight and then was filtered to yield 0.48 g of white, solid residue, which on C, H, N analysis was consistent with the formula Me$_6$Xyl(en)$_2$.[ZnSO$_4$]$_2$.ZnSO$_4$.7H$_2$O.

The filtrate was evaporated to a sludge which on trituration with dioxolane gave a white solid (1.53 g) which exhibited no sharp melting point on heating and which appeared virtually insoluble in D$_2$O, dimethylsulfoxide and acetone-d$_6$.

Analysis: Calc. for C$_{18}$H$_{34}$N$_4$S$_2$O$_8$Zn$_2$, MW 629.359; C 34.35%, H 5.45%, N 8.90%, S 10.19%, Zn 20.77% Found: C 33.68%, H 5.73%, N 8.63%, S 10.08%.

NMR Spectrum (CD₃OD-TMS): δ 7.98 (broad singlet, aromatic proton, 1H); δ 7.36 (broad singlet, aromatic protons, 3H); δ 4.83 (singlet, OH, ca. 7H); δ 3.91 (apparent doublet, benzylic protons, 4H); δ 3.34 (broad singlet, residual methanol protons, ca. 5H); δ 2.93, 2.67, and 2.37 (broad singlets, NCH₂ and NCH₃, 26H).

This example demonstrates that acyclic binucleating ligands herein form stoichiometric adducts with two equivalents of divalent metal salts. The complex so prepared may be mixed with a complex containing Cu(I) so as to obtain a complex useful in homogeneous catalysis.

In summary, the present invention is seen to provide a complex of at least two metals, one of which is Cu(I), and a binucleating ligand containing at least four donor sites selected from N, O and S atoms. The ligand confers significant stability to the ionic metallic site and allows sufficient metal vacancies so as to promote interaction of small molecules such as CO.

What is claimed is:

1. A complex coordinated with carbon monoxide comprising a salt of a cation and an anion, said cation consisting of two atoms of the same metal complexed with a polydentate binucleating ligand of the formula:

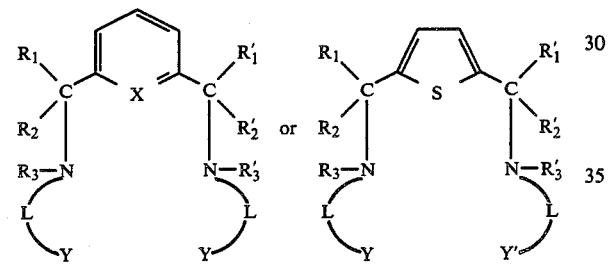

where X is CH, Y and Y' are independently selected from the group consisting of —OH, —NH₂, —NHR, —NR₂, and NR where R is a saturated alkyl or saturated alkylene radical, R₁, R₂, R₃, R'₁, R'₂ and R'₃ are independently —H, —CH₃ or —CH₂CH₃, and L is —CH₂CH₂—, —CH₂CH₂CH₂—,

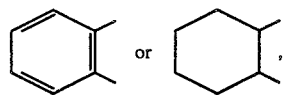

wherein said metal is selected from the group consisting of Li, Na, Sc, Ti, V, Cr, Mn, Fe, Co, Ni, Cu, Zn, Ru, Rh, Pd, Ag, Cd, Os, Ir and Pt, and wherein the anion of the salt is Cl⁻, NCS⁻, SO₄⁻², B(C₆H₅)₄⁻, C₆H₅CO₂⁻, CH₃CO₂⁻ a mixture of any of these anions.

2. The complex of claim 1 wherein said metal is selected from the group consisting of Li, Na, Fe, Co, Ni, Cu, Zn, Ru, Rh, Pd, Ag, Cd, Os, Ir, and Pt.

3. The complex of claim 1 wherein said metal is selected from the group consisting of Fe, Co, Ni, Cu, Pd and Pt.

4. The complex of claim 1 wherein said metal is copper.

5. The complex of claim 1 wherein the ligand is of the formula:

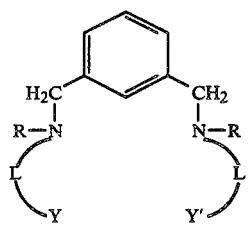

where R is —H or —CH₃, L is —CH₂CH₂— or —CH₂CH₂CH₂—, and Y and Y' are —NH₂, —NH(CH₃) or —N(CH₃)₂.

6. The complex of claim 5 wherein said metal is copper.

7. The complex of claim 1 wherein the ligand is 1,3-bis-(2,5-diaza-2,5-dimethylhexyl) benzene or 1,3-bis-(2,6-diaza-2,6-dimethylheptyl) benzene.

8. The complex of claim 7 wherein said metal is copper and the anion of the salt is selected from the group consisting of Cl⁻, B(C₆H₅)₄⁻, C₆H₅CO₂⁻ and CH₃CO₂⁻.

* * * * *